US010292592B2

(12) United States Patent
Marshall et al.

(10) Patent No.: US 10,292,592 B2
(45) Date of Patent: May 21, 2019

(54) METHOD AND APPARATUS FOR OPTICAL RECORDING OF BIOLOGICAL PARAMETERS IN FREELY MOVING ANIMALS

(71) Applicant: The Board of Trustees of the Leland Stanford Junior University, Palo Alto, CA (US)

(72) Inventors: Jesse D. Marshall, Menlo Park, CA (US); Mark J. Schnitzer, Palo Alto, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 860 days.

(21) Appl. No.: 14/939,637

(22) Filed: Nov. 12, 2015

(65) Prior Publication Data

US 2016/0135754 A1 May 19, 2016

Related U.S. Application Data

(60) Provisional application No. 62/079,118, filed on Nov. 13, 2014.

(51) Int. Cl.
*A61B 5/00* (2006.01)

(52) U.S. Cl.
CPC .......... *A61B 5/0071* (2013.01); *A61B 5/4064* (2013.01); *A61B 2503/40* (2013.01)

(58) Field of Classification Search
None
See application file for complete search history.

(56) References Cited

U.S. PATENT DOCUMENTS

| 6,049,727 A * | 4/2000 | Crothall | A61B 5/14532 600/310 |
| 6,258,576 B1 * | 7/2001 | Richards-Kortum | A61B 5/0059 425/288 |
| 8,788,021 B1 * | 7/2014 | Flusberg | A61B 5/0059 356/318 |

(Continued)

FOREIGN PATENT DOCUMENTS

CA    2809581 A1    3/2012

OTHER PUBLICATIONS

Cardin, et al., "Targeted optogenetic stimulation and recording of neurons in vivo using cell-type-specfic expression of Channelrhodopsin-2", "Nature Protocols;", Jan. 21, 2010, pp. 247-254, No. 5, Publisher: nature publishing group; http://www.nature.com/nprot/journal/v5/n2/full/nprot.2009.228.html; doi:10.1038/nprot.2009.228; ISSN: 1754-2189.

(Continued)

*Primary Examiner* — Paul A D'Agostino
(74) *Attorney, Agent, or Firm* — Kaplan Breyer Schwarz, LLP

(57) ABSTRACT

A system and method for monitoring biological parameters in freely moving animals that, in the illustrative embodiment, comprises a two-color optical measurement/recording system that is combined with a fluorescent protein reporter of cellular membrane potentials and a fluorescent protein that is insensitive to such cellular membrane potentials. The two wavelengths are used to un-mix physiological artifacts in recordings that occur in freely moving animals.

20 Claims, 10 Drawing Sheets

(56) References Cited

U.S. PATENT DOCUMENTS

| | | | | |
|---|---|---|---|---|
| 9,107,575 | B2* | 8/2015 | Boularot | A61B 1/00154 |
| 2004/0122301 | A1* | 6/2004 | Kiani | A61B 5/14535 600/336 |
| 2007/0016078 | A1* | 1/2007 | Hoyt | A61B 5/0059 600/476 |
| 2007/0060811 | A1* | 3/2007 | Roberts | A61B 5/1459 600/332 |
| 2009/0163783 | A1* | 6/2009 | Mannheimer | A61B 5/02416 600/306 |
| 2010/0049023 | A1* | 2/2010 | Sterling | A61B 5/14551 600/363 |
| 2010/0280348 | A1* | 11/2010 | Wenzel | A61B 5/0452 600/365 |
| 2010/0292549 | A1* | 11/2010 | Shuler | A61B 5/0215 600/324 |
| 2010/0317943 | A1* | 12/2010 | Kuhn | A61B 5/1459 600/323 |
| 2011/0004069 | A1* | 1/2011 | Ochs | A61B 5/02416 600/300 |
| 2011/0261175 | A1 | 10/2011 | Fomitchov et al. | |
| 2011/0282181 | A1* | 11/2011 | Wang | A61B 5/0095 600/407 |
| 2012/0022337 | A1* | 1/2012 | Hyde | A61K 35/17 600/301 |
| 2012/0184560 | A1* | 7/2012 | Wong | G01N 33/57407 514/252.19 |
| 2012/0184813 | A1* | 7/2012 | Terakawa | A61B 1/00009 600/109 |
| 2012/0283535 | A1* | 11/2012 | Sarussi | A61B 5/02416 600/324 |
| 2012/0323112 | A1* | 12/2012 | Jokerst | A61K 49/225 600/420 |
| 2013/0102865 | A1* | 4/2013 | Mandelis | A61B 5/0095 600/328 |
| 2013/0109941 | A1* | 5/2013 | Li | G01N 21/1702 600/364 |
| 2013/0165734 | A1* | 6/2013 | Butters | A61N 2/002 600/13 |
| 2013/0169759 | A1* | 7/2013 | Godavarty | A61B 5/0073 348/47 |
| 2015/0031971 | A1* | 1/2015 | Lisogurski | A61B 5/14552 600/324 |
| 2015/0148630 | A1* | 5/2015 | Meester | A61B 1/00009 600/317 |

OTHER PUBLICATIONS

Cui, et al., "Deep brain optical measurements of cell typespecific neural activity in behaving mice", "Nature Protocols", May 1, 2014, pp. 1213-1228, No. 9, Publisher: nature publishing group; ISSN: 1754-2189; doi:10.1038/nprot.2014.080.

Ferezou, et al., "Visualizing the Cortical Representation of Whisker Touch: Voltage-Sensitive Dye Imaging in Freely Moving Mice", "Science Direct; Neuron", May 18, 2006, pp. 617-629, vol. 50, No. 4, Publisher: Cell Press under Elsevier; doi:10.1016/j.neuron.2006.03.043.

Flusberg, et al., "Fiber-optic fluorescence imaging", "Nature Methods", Dec. 2005, pp. 941-950, vol. 2, Publisher: nature publishing group; doi:10.1038/nmeth820; ISSN: 1548-7091.

Peterka, et al, "Imaging Voltage in Neurons", "Neuron Primer", Jan. 13, 2011, pp. 9-21, vol. 69, Publisher: Elsevier Inc.; DOI 10.1016/j.neuron.2010.12.010.

Wilt, et al., "Advances in Light Microscopy for Neuroscience", "The Annual Review of Neuroscience", 2008, pp. 435-506, No. 32, Publisher: Annual Reviews; doi; 10.1146/annurev.neuro.051508.135540.

* cited by examiner

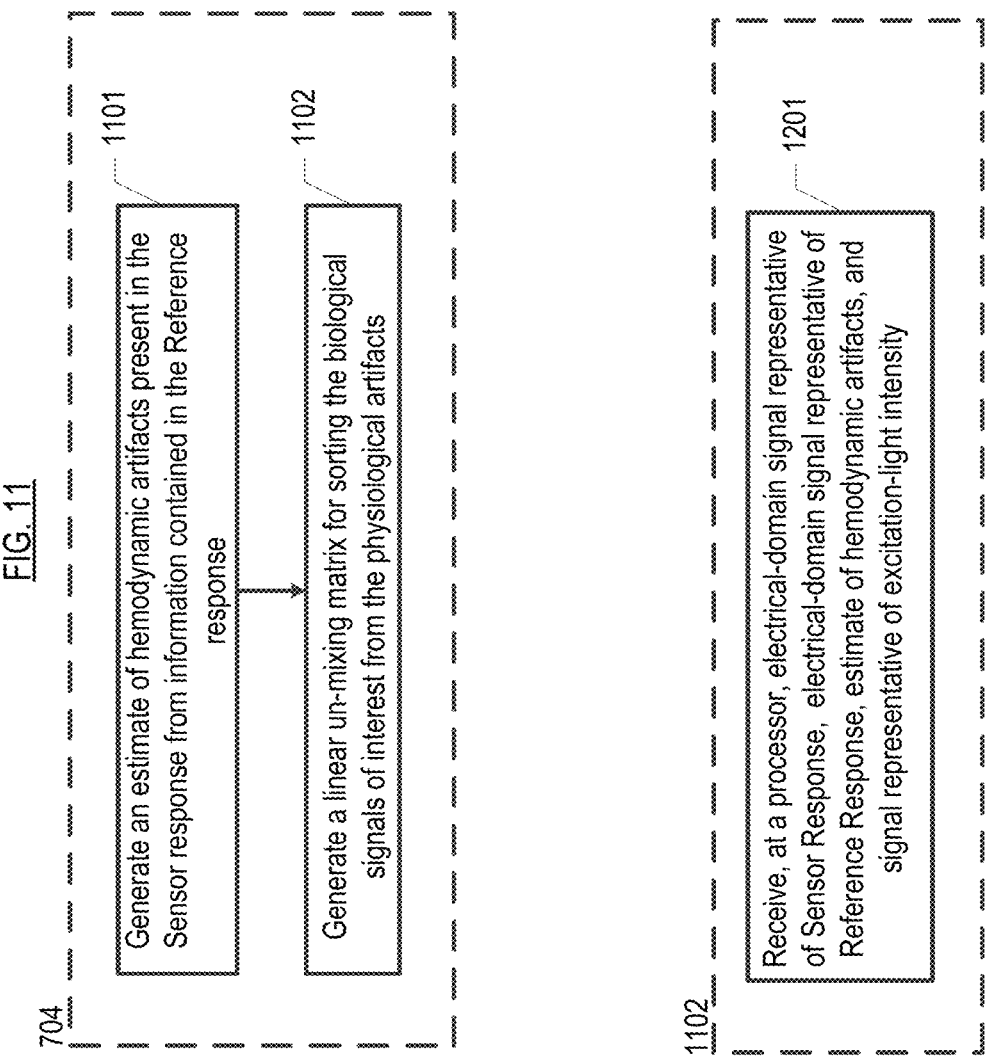

METHOD AND APPARATUS FOR OPTICAL RECORDING OF BIOLOGICAL PARAMETERS IN FREELY MOVING ANIMALS

STATEMENT OF RELATED CASES

This case claims priority to U.S. Pat. Application 62/079,118, filed Nov. 13, 2014 and which is incorporated by reference herein. U.S. Pat Application 62/253,294, filed Nov. 10, 2015, is incorporated by reference herein.

FIELD OF THE INVENTION

The present invention relates to the measurement of biological processes in freely moving animals.

BACKGROUND OF THE INVENTION

Measurements of extracellular electric field potentials are widely used in clinical diagnostics and across a broad range of research contexts in cognitive psychology, neurophysiology, and systems neuroscience. Different forms of electroencephalographic (EEG) oscillations and event-related potentials are indicative of various brain states that are associated with distinct behaviors, modes of cognition and disease. In most cases, however, the physiological origins, functional importance and computational roles of electrical potential dynamics and their intracellular correlates remain unclear.

Extracellular field potentials generally reflect the combined dynamics of multiple cell types and electrophysiological mechanisms across a broad range of length scales. This mechanistic complexity has precluded general cell biological interpretations of both normal and pathological electric field oscillations, especially in deep-brain regions. Laminar brain structures such as the mammalian cortex and hippocampus permit charge source density analyses that have allowed some empirical dissections of the electrical sources and sinks in different tissue layers. These analyses are, however, generally uninformative in non-laminar brain structures such as the striatum that contain intermingled, heterogeneous cell types.

What is needed in the art is a tool capable of measuring biological parameters, such as trans-membrane potential dynamics, in a cell-type specific manner, in actively behaving animals. Electrophysiological approaches for measuring intracellular voltage dynamics are usually limited to recordings in single cells and are also nearly prohibitive to perform in a manner that targets specific cell types in behaving animals, especially in sub-cortical brain areas. By comparison, optical techniques for recording the dynamics of large populations of specific neuron-types can work well in behaving animals, via targeted expression of fluorescent protein indicators of intracellular Ca' concentration. However, intracellular $[Ca^{2+}]$ is an indirect correlate of membrane depolarization, is a poor proxy of spiking activity in many cell types, tracks neither subthreshold, inhibitory, nor oscillatory neural activity well, and does not report fast dynamics on timescales finer than about 25 to 50 milliseconds. These limitations preclude the use of $Ca^{2+}$ indicators as a general means of tracking large-scale brain oscillatory dynamics in live mammals.

In contrast to these established approaches, genetically encoded fluorescent indicators of membrane voltage directly report both sub-threshold and inhibitory trans-membrane voltage activity. Such indicators therefore provide a possible means of tracking neural membrane potentials in a cell-type specific way in behaving animals. Several prior studies have used either synthetic or genetically encoded fluorescent voltage indicators to monitor sensory evoked potentials in the rodent neocortex. Other optical studies have tracked neocortical voltage oscillations in rodents under or in recovery from anesthesia. However, even the most sensitive existing protein voltage indicators offer modest signaling dynamic ranges; that is, about 1% fluorescence changes ($\Delta F/F$) per 10 mV voltage change in vitro and about 0.5% when averaged across a population in vivo. These amplitudes are comparable to the dynamic ranges of hemodynamic and brain motion artifacts that arise in vivo: about 1% optical fluctuations across 0.1-15 Hz bandwidth. Even in anesthetized animals, sufficient elevation of genetically-encoded voltage signals above physiological noise sources has thus required a combination of single trial averaging and the use of less-sensitive, two-color FRET voltage sensors to reduce physiological artifacts.

An even more persistent obstacle to the use of both genetically-encoded and synthetic fluorescent voltage sensors is recording noise introduced by photon-shot noise. That is, the intrinsic fluctuations in optical experiments introduced by the randomness of photon emission and detection processes. The relative variance of shot noise in optical recordings is inversely proportional to the light intensity. Photobleaching rates depend exponentially on illumination power, which has generally limited recording lengths to tens of seconds to several minutes. No prior optical system has had the detection sensitivity needed to overcome the shot noise and physiological artifacts that are unavoidably present in optical recordings in unrestrained animals and to monitor voltage oscillations in freely behaving mammals.

SUMMARY OF THE INVENTION

The invention provides a system and method for monitoring biological parameters in freely moving animals. The illustrative embodiment provides a system and method for monitoring the aggregate depolarizing and hyperpolarizing trans-membrane voltage dynamics of genetically specified neurons in freely moving animals.

In accordance with the illustrative embodiment, membrane potential in freely-moving animals is read using a two-color optical measurement/recording system that is combined with a fluorescent protein reporter of cellular membrane potentials and a fluorescent protein that is insensitive to such cellular membrane potentials. The two wavelengths are used to un-mix physiological artifacts in recordings that occur in freely moving animals.

In the illustrative embodiment, two adeno-associated viral vectors (AAV2/5-CaMKIIα-MacQ-mCitrine and AAV2/5-CaMKIIα-mCherry) were co-injected into target tissue (mouse somatosensory neocortex) to deliver the (green) fluorescent voltage indicator and red fluorescent reference fluor to pyramidal neurons therein.

In the illustrative embodiment, the optical measurement/recording system includes two single-mode, fiber-coupled lasers, one of which at 488 nm and the other at 561 nm. The lasers are amplitude-modulated by a function generator and optically coupled into a fiber-optic cable. In accordance with the illustrative embodiment, to reduce low frequency noise, the laser sources are amplitude modulated at 900 Hz and all optical signals are read-out via lock-in amplifiers. To reduce cross talk, the 561 nm laser source is phase-shifted (e.g., 90 degrees, etc.).

The intensity of each laser is monitored via photodetectors, which, in the illustrative embodiment, are photodiodes. A multi-mode fiber-optic cable, having a core diameter matched to that of the excitation light from the lasers, is optically coupled to an optical fiber that is implanted in the brain of the subject animal. The lasers excite fluorescence in the brain, which is collected via the same optical fiber. The collected fluorescence is separated into red and green components and directed to the two photodetectors.

To correct the neural signal for physiologically induced artifacts, such as hemodynamic, respiration-related, and motion-induced artifacts, voltage sensor fluorescence (green) and red fluorescence generated by a non-voltage sensitive fluorophore is simultaneously monitored. A novel two-stage un-mixing methodology that incorporates independent component analyses ("ICA") is used to separate the neural signals from the artifacts.

Numerous optical systems permit freely moving recordings of neuronal activity, but most have only demonstrated an ability to monitor fluorescent sensors of intracellular $Ca^{2+}$. Fluorescent reports of intracellular $Ca^{2+}$ dynamics have large dynamic range (>15% $\Delta F/F$ for calcium transients in vivo) across slow timescales (~1 to 2 seconds), making them a readily accessible correlate of neuronal activity. But measurements of intracellular $Ca^{2+}$ are indirect, not suitable for use in all cell types, and do not track sub-threshold or inhibitory neural activity of fast timescales.

Although genetically encoded sensors of membrane voltage offer a direct readout of sub-threshold and inhibitory neural dynamics, existing sensors offer low signal-to-noise (~1% $\Delta F/F$ 10 mV fluctuations characteristic of high-amplitude oscillations) in comparison to the sizable hemodynamic and motion artifacts that occur in vivo (~0.5 to 1% across 0.1 to 15 Hz). No prior-art optical system has shown the ability to correct for these noise sources and monitor genetically-encoded sensors of membrane voltage in freely moving animals.

In an optical measurement/recording system in accordance with the illustrative embodiment, the drawbacks of the prior art are addressed via a number of innovations that enables near shot-noise limited optical recordings of cell type specific trans-membrane voltage dynamics in freely-moving animals achieving <0.1% $\Delta F/F$ sensitivity with broad temporal bandwidth (1 to 50 Hz). The innovations include:

i. The use of a reference channel to monitor physiological artifacts in freely moving animals and facilitate their "extraction" from the neural signal.

ii. The development and use of a two-stage blind source un-mixing procedure to—"separate" physiological artifacts from the neural signal in conjunction with the reference channel.

iii. The use of phase-multiplexed amplitude-modulation of excitation sources to remove flicker noise and practical minimize cross-talk between excitation sources (when multiple sources are present).

iv. The use of single-mode excitation sources to prevent auto-fluorescence due to the excitation of fiber cladding modes. Multimode optical fiber offers high numerical aperture ("NA"), but auto-fluorescence generation and bending-induced artifacts during animal behavior can be problematic. In the illustrative embodiment, a flexible 0.39 NA fiber with 400 micron core diameter was used in conjunction with 5-axis alignment of single-mode excitation lasers to reduce auto-fluorescence generated in the polymer cladding to an order of magnitude below signal levels.

v. The use of photodetectors enables high collection powers (>5 nW). But they suffer from prominent low-frequency noise. In the illustrative embodiment, that is addressed via an amplitude-modulating optical source(s) and a lock-in amplifier.

As compared to the prior art, embodiments of the present invention provide the following benefits, among others:

first system and method to simultaneously optically monitor membrane potentials and artifacts in freely moving animals;

efficient artifact removal, thereby enabling measurements with 10-fold improved sensitivity compared to the prior art;

an ability to be used in conjunction with freely moving animals exhibiting complex animal behaviors;

spatial localization; that is, an ability to identify specific spatial regions of neuronal oscillations, which is not possible with prior-art systems;

genetic specificity; that is, an ability to monitor neuronal oscillations in specific cell types;

subcellular specificity; that is, an ability to identify neuronal oscillations in specific subcellular compartments;

an ability to record subthreshold and hyperpolarizing neuronal activity, not possible with optical recordings of intracellular calcium; and suitability for measuring and recording membrane voltage of both superficial and deep-brain regions.

BRIEF DESCRIPTION OF THE DRAWINGS

FIG. 11 depicts tasks for implementing step 704 of the method of FIG. 7.

FIG. 12 depicts a sub-task for implementing one of the tasks shown in FIG. 11.

DETAILED DESCRIPTION

Figure 1:
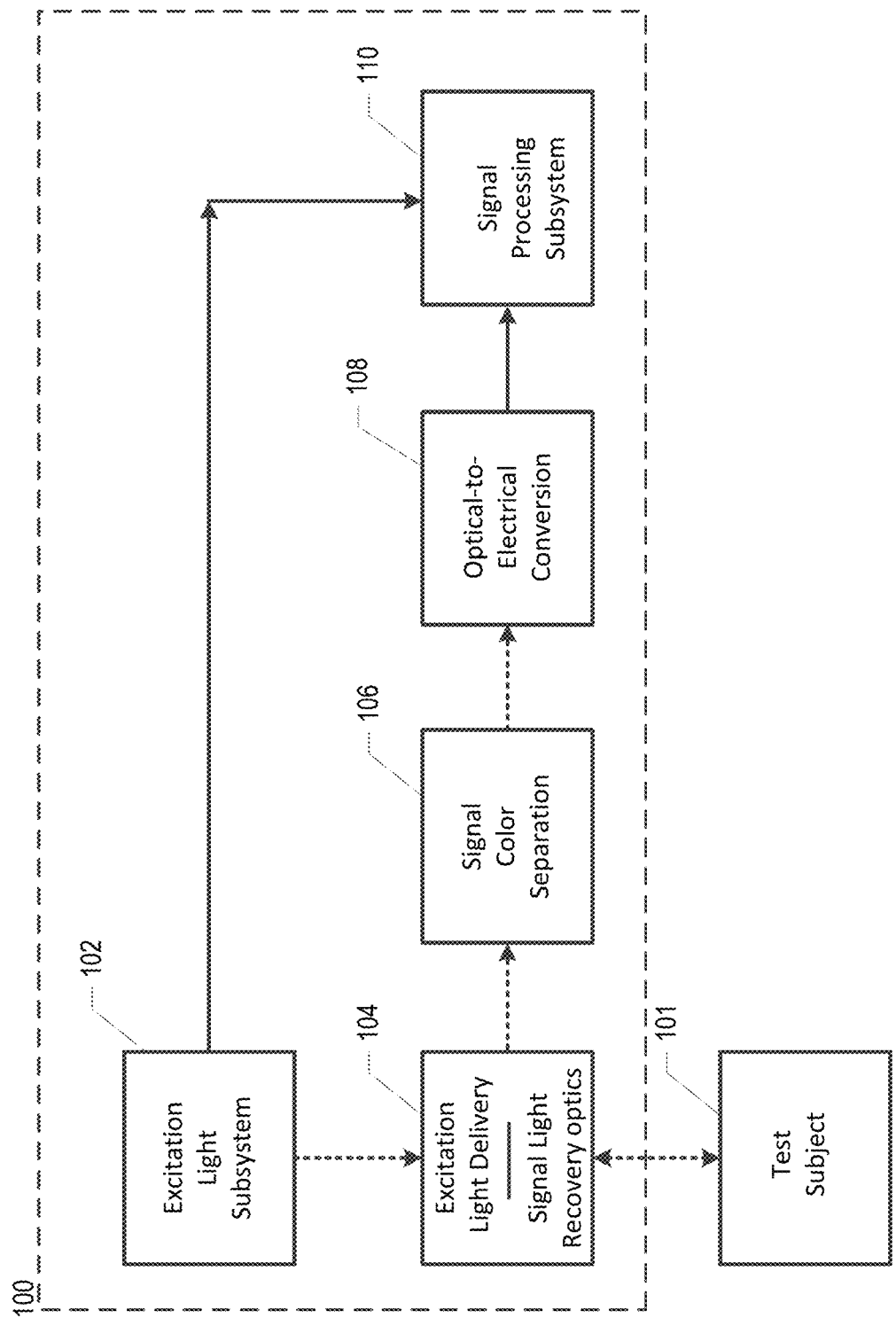
FIG. 1 depicts an embodiment of an optical measurement/recording system in accordance with the present teachings.

In accordance with the present invention, a system and method is provided for monitoring a biological parameter of a freely moving animal. The biological parameter can be indicative of a biological process of interest (i.e., neural processing, etc.). In the illustrative embodiment, the biological parameter is the membrane potential (membrane voltage) of neurons. In some other embodiments, the biological parameter can be, without limitation, pH, or concentrations of intracellular or extracellular calcium, or other ions such as zinc or copper, concentrations biomolecules, peptides and proteins such as neurotransmitters, hormones, neuro-modulatory peptide or molecules, transcription factors, and intracellular or intraorganelle signaling molecules, other properties of said biomolecules and peptides such as phosphorylation or ligand binding or conformation, the concentration or other properties of synthetic molecules and peptides such as small molecule pharmaceuticals and biologicals. In experiments conducted using the present system, the animal was a mouse. However, in some other embodiments, the target animal can be, for example and without limitation, a rat, a human, an invertebrate, or a transgenically modified organism. And in some embodiments, rather than measuring a biological parameter of neurons, the target cells can be, without limitation, muscle cells, glia, ips cells, cardiomyocytes, etc.

The biological parameter of interest is monitored by a "sensor." In the illustrative embodiment of the invention, membrane voltage is monitored via an optical voltage sensor. The optical voltage sensor transduces a change in membrane voltage into a change in an optical property of the sensor. In accordance with the illustrative embodiment, the sensor is a fluorescent protein. For the fluorescent proteins used in the illustrative embodiment, bioelectrical activity, such as a change in membrane voltage, modulates the fluorescence absorption coefficient (efficiency of photon uptake) or the fluorescence emission coefficient (efficiency of photon emission) of the fluorescent protein. When illuminated by appropriate excitation light, more or less fluorescence is emitted by the fluorescent protein (relative to a baseline amount that is obtained when the animal is resting) as a function of the electrical activity.

It will be appreciated by those skilled in the art that a variety of other types of sensors are available to monitor changes in membrane voltage. For example, in terms of optical modality, sensors that respond to a voltage change by linear or non-linear changes in the fluorescence, luminescence, transmission, absorbance, polarization and spectral properties, or phase contrast, among others, are available. Furthermore, with respect to a given optical modality, sensors can differ in terms of the mechanism by which a voltage change leads to a change in a particular optical property. Additionally, the sensor can be in the form of a dye, RNA, endogenously fluorescent or luminescent molecule, inorganic nanoparticle, organic particle, among others. In light of this disclosure, it will be within the capabilities of those skilled in the art to adapt embodiments of the present invention to utilize such other types of sensors.

As previously noted, attempts to monitor the cellular activity of freely moving animals is complicated by the presence of certain artifacts, both physiological and otherwise. In accordance with the present teachings, this issue is addressed via the use of a second "reference" channel. In accordance with the illustrative embodiment, two fluorescent proteins, one of which (the "sensor") is responsive to the biological parameter of interest—membrane voltage in the illustrative embodiment—and the second of which (the "reference") is not. However, both fluorescent proteins are responsive to the artifacts. Thus, as used in this disclosure and the appended claims, the term "sensor" refers to something that is sensitive to a biological parameter of interest and the term "reference" refers to something that is insensitive to the biological parameter of interest, and further wherein both the sensor and reference are sensitive to the same physiological artifacts.

Figure 6:
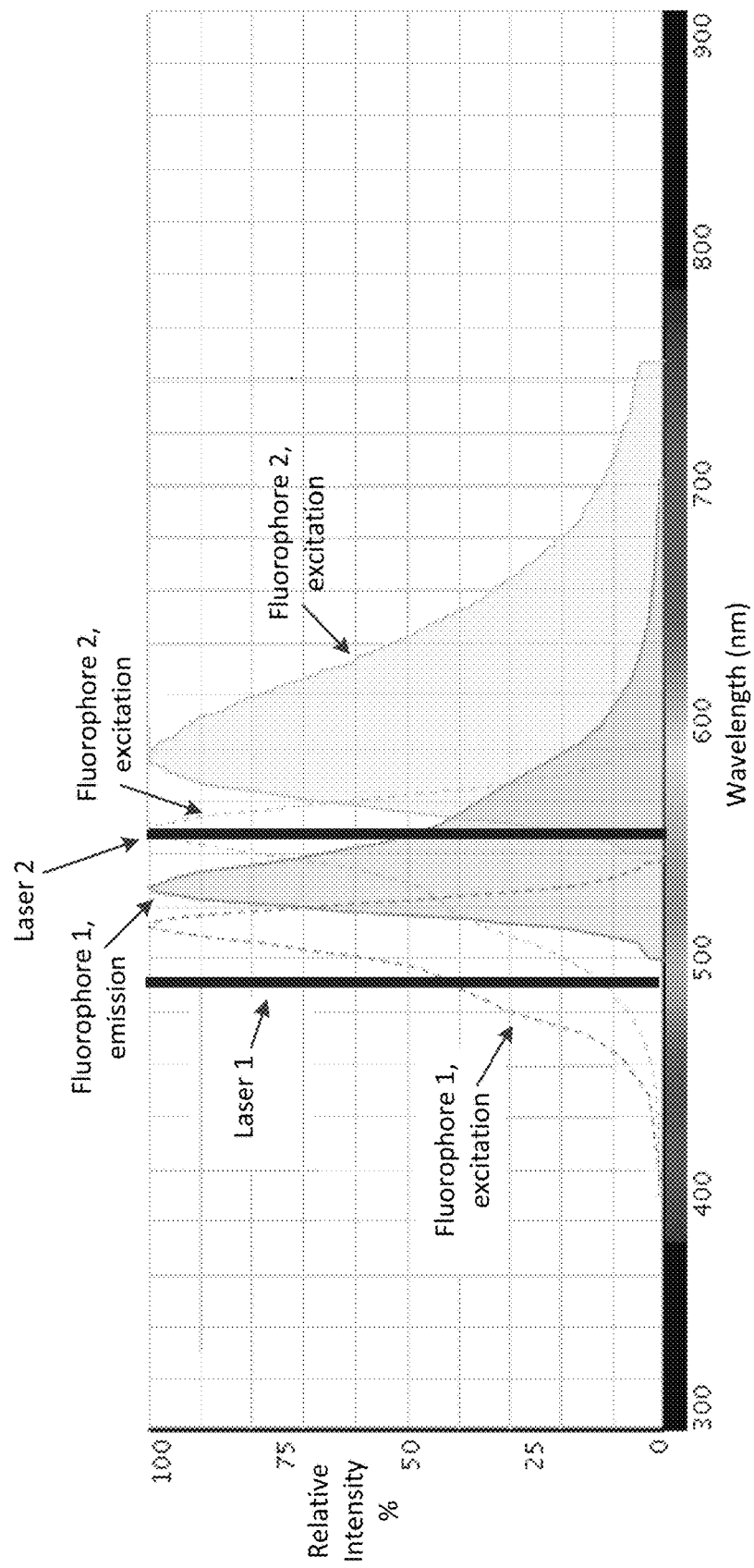
FIG. 6 depicts an illustrative arrangement of sensor and reference fluors for use in conjunction with some embodiments of the present invention.

FIG. 6 depicts an example arrangement of sensor and reference for use in conjunction with some embodiments of the present invention. Two fluorescent proteins, identified as "Fluorophore 1" and "Fluorophore 2" with non-identical excitation and emission spectra are depicted. FIG. 6 shows the respective excitation and emission wavelengths for the two fluorophores. As depicted, Fluorophore 1 has peak in excitation intensity at about 510 nm and a peak in emission intensity at about 525 nm. Fluorophore 2 has a peak in excitation intensity at about 540 nm and a peak in emission intensity at about 590 nm. The excitation band of laser 1 is at about 490 nm and the excitation band of laser 2 is at about 540 nm. The Figure also shows possible excitation bands of two lasers.

It will be appreciated that many instances of the sensor (e.g., many molecules of the selected voltage-sensitive fluorescent protein, etc.) and many instances of the reference will be delivered to the target tissue. However, for convenience, the singular and plural version of "sensor" and "reference" will be used interchangeably herein.

In some other embodiments, more than one type of sensor and/or more than one type of reference is used to monitor the same or different biological parameters and the same or different artifacts in the same tissue. Various methodologies can be used for introducing the sensor and reference (whether fluorescent proteins or other types) into tissue, such as viral transduction, electroporation, bolus loading, and ballistic injection among others, may suitably be used.

In the illustrative embodiment, fluorescent emissions are collected from the region of interest and analyzed. The collected fluorescence contains information (1) pertaining to membrane voltage, as obtained via the sensor and, (2) information pertaining to various artifacts, including physiological-based artifacts such as cardiac artifacts and movement-based artifacts, as obtained via the reference (and the sensor).

A novel two-stage, blind-source separation algorithm was developed by the inventors to separate the biological parameter of interest (i.e., trans-membrane voltage) from the physiological and/or other artifacts. The ability to separate out the biological parameter of interest from the artifacts greatly increases the sensitivity of the system (c.a. 10-fold better sensitivity than prior recording technologies for use with freely moving animals), enabling recording sessions of up to about an hour, compared with only a few minutes for the prior art.

FIG. 1 depicts a block diagram of optical measurement/recording system 100 for measuring membrane potentials in freely-moving animal 101, in accordance with the illustrative embodiment of the present invention. System 100 includes excitation-light subsystem 102, excitation-light delivery/signal recovery optics 104, signal color separation 106, optical-to-electrical conversion 108, and signal processing subsystem 110.

In the illustrative embodiment, excitation-light subsystem 102 generates excitation light, at least a portion of which is delivered to a sensor-laden region in an animal. In some embodiments, excitation-light subsystem 102 includes circuitry/devices for modulating, phase shifting, etc., the excitation light. Excitation-light subsystem 102 is discussed in further detail in conjunction with FIGS. 2A and 2B.

In embodiments of the invention, excitation-light delivery/signal recovery subsystem 104 provides two primary functions:
- direct light (e.g., red and green light, etc.) to a region of test subject 101 to excite the sensor(s) and reference(s) introduced to that region;
- collect an optical response from the sensor(s) and reference(s).

Figure 3:
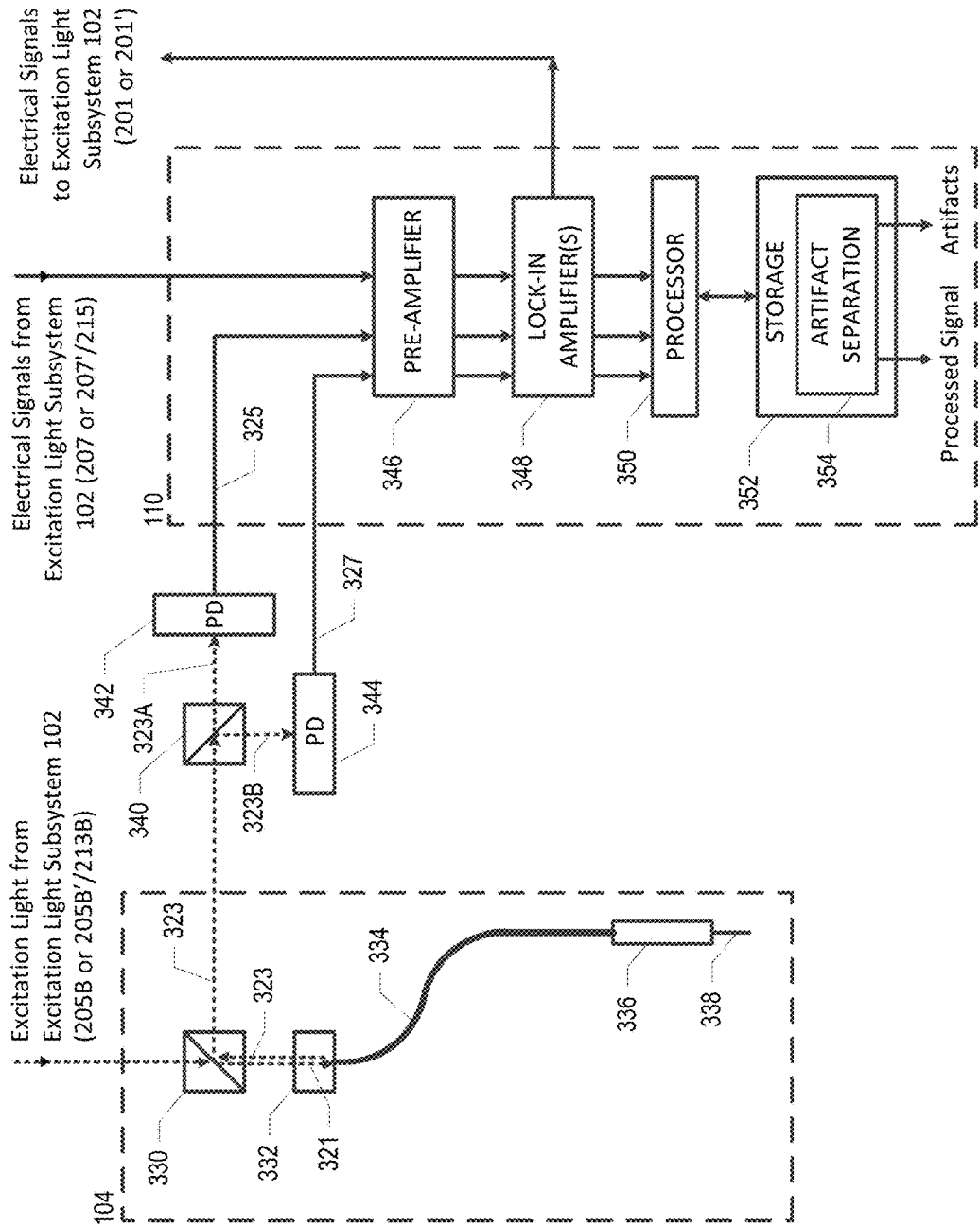
FIG. 3 depicts an embodiment of various other subsystems of the optical measurement/recording system of FIG. 1.

Excitation-light delivery/signal recovery optics 104 is discussed in further detail in conjunction with FIG. 3.

Signal color separation 106 separates the collected light into constituent colors. In the illustrative embodiment, the collected fluorescence is separated into two colors: red and green. Signal color separation 106 is discussed further in conjunction with FIG. 3. The separated light is converted into a corresponding electrical signal(s) at optical-to-electrical conversion 108. Optical-to-electrical conversion 108 is discussed in further detail in conjunction with FIG. 3.

The electrical signal(s) corresponding to the collected fluorescence are delivered to signal processing subsystem 110. The signal processing subsystem separates the physiological and other artifacts from the signal of interest (e.g., the neural signal, etc.). Also, aspects of the signal processing subsystem 110 are used to pre-process the excitation light. Signal processing subsystem 110 is discussed further in conjunction with FIGS. 2B, 3, 5A, and 5B.

Figure 7:
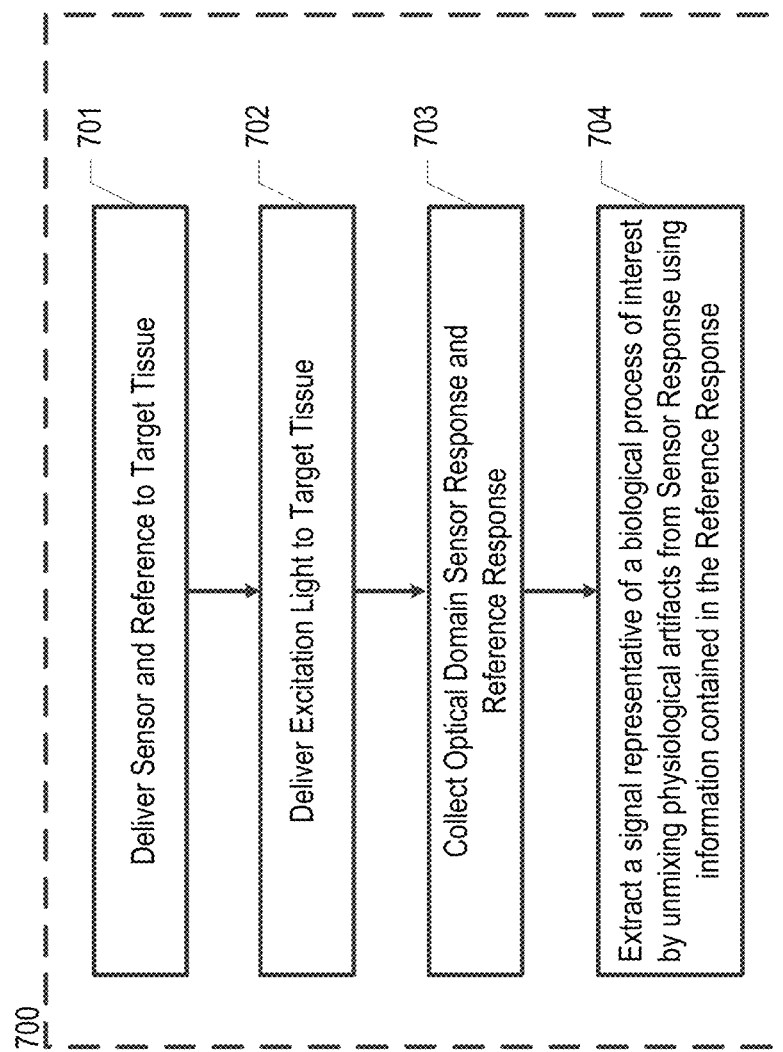
FIG. 7 depicts a method in accordance with the present teachings.

FIG. 7 depicts method 700 in accordance with the illustrative embodiment of the invention. Per step 701, sensor(s) and reference(s) are delivered to the target tissue. In the illustrative embodiment, the sensor(s) and reference(s) are two different fluorescent proteins (see, e.g., FIG. 6, etc.) that are introduced into the brain via viral transduction. Although, as previously indicated, other types of sensors and references, and other techniques for introducing same into or near to the target tissue, may suitably be used.

In accordance with step 702, excitation light is delivered to the target tissue. This step is discussed in further detail in conjunction with FIGS. 2A, 2B, 3, 4, 8, 9A, and 9B and the accompanying discussion.

In step 703, the optical domain sensor response and reference response is collected. In the illustrative embodiment, this involves capturing the fluorescence emitted from the sensors and references into a waveguide (e.g., optical fiber, etc.). This step is discussed in further detail in conjunction with FIGS. 3, 4, and 10 and the accompanying discussion.

In accordance with step 704, a signal representative of a biological parameter of interest is extracted from the sensor response by un-mixing various physiological artifacts, which are present in the sensors' response, using information contained in the references' response. This step is discussed in further detail below in conjunction with FIGS. 3, 5A, 5B, 11, and 12 and the accompanying discussion.

Figure 2:
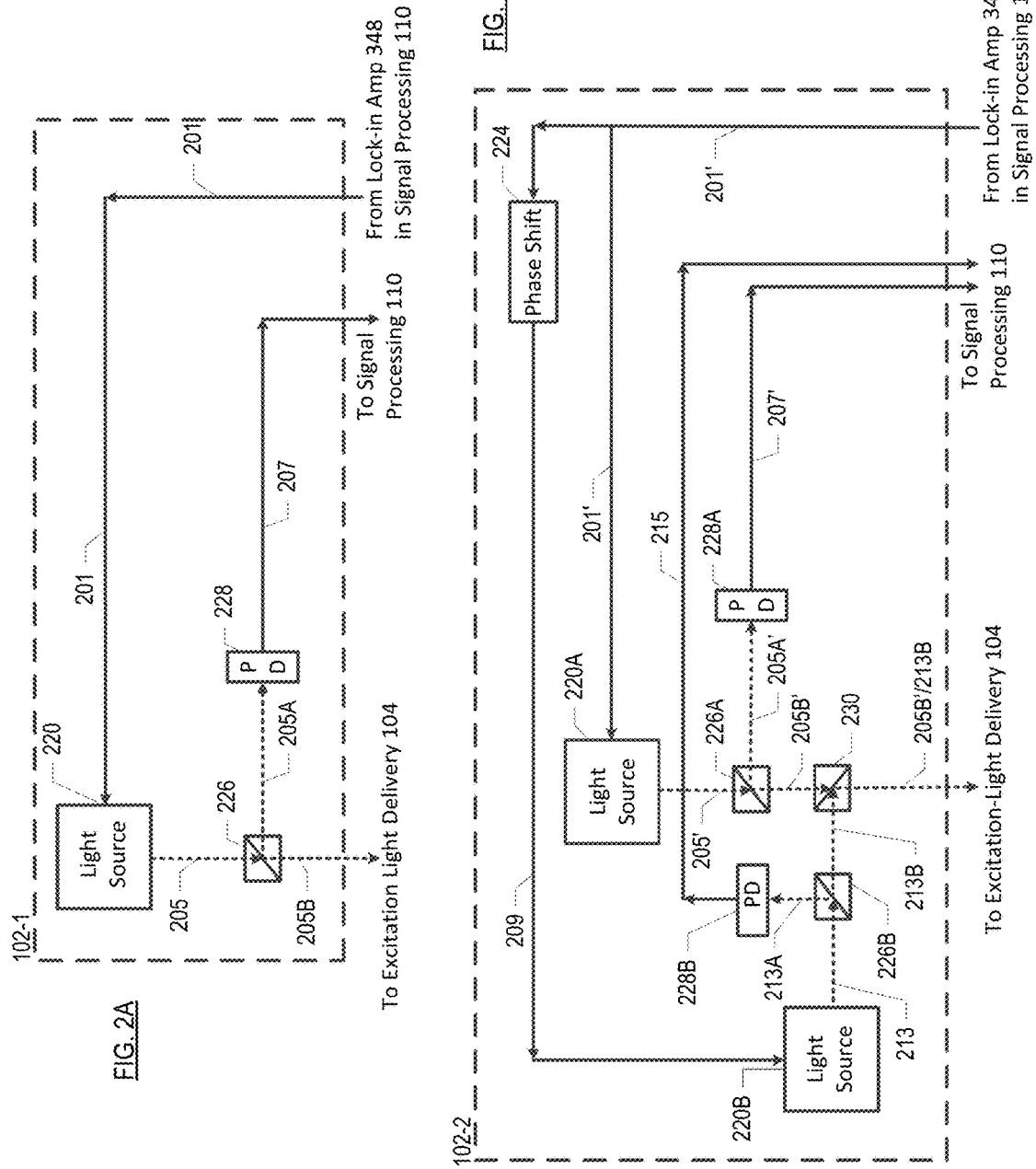
FIG. 2A depicts a first embodiment of the excitation light subsystem of the optical measurement/recording system of FIG. 1.
FIG. 2B depicts a second embodiment of the excitation light subsystem of the optical measurement/recording system of FIG. 1.

FIG. 2A depicts a first embodiment of an excitation-light subsystem in accordance with the present teachings. Subsystem 102-1 includes a single excitation-light source 220, beam splitter 226, and photodetector 228 in a free-space-optics arrangement and interrelated as shown.

Light source 220 generates light 205. In this embodiment, light source 220 is a laser, although other sources of light may suitably be used in combination with a filter, etc., as appropriate, to provide a narrow-band source. Light source 220 is modulated by signal 201, which is generated by one of lock-in amplifiers 348 in signal processing subsystem 110. Pre-processing light 205 in this fashion reduces low-frequency noise in the measurement of fluorescence at photodetectors 342 and 344 (see FIG. 3).

Light 205 is directed to beam splitter 226, wherein, in the illustrative embodiment, it is divided 50/50 in intensity. Portion 205A of light 205 is directed to photodetector 228, which generates corresponding electrical-domain signal 207. Electrical-domain signal 207 is directed to signal processing system 110 and is used as a measure of the intensity of the excitation light during signal processing. Portion 205B is directed to excitation-light delivery/signal recovery subsystem 104. Portion 205B is the light that will illuminate the region of interest in test subject 101.

FIG. 2B depicts a second embodiment of an excitation-light subsystem in accordance with the present teachings. Subsystem 102-2 includes light sources 220A and 220B, phase shifter 224, beam splitters 226A, 226B, 230, and photodetectors 228A and 228B.

Light source 220A generates light 205'. In this embodiment, light source 220A is a laser, although other sources of light may suitably be used in combination with a filter, etc., as appropriate, to provide a narrow-band source. In the illustrative embodiment, Light 205' is modulated at a single frequency by signal 201', which is generated by one of lock-in amplifiers 348 in signal processing subsystem 110.

Light source 220B generates light 213 having a different wavelength than light 205'. Light 213 is modulated at a single frequency by signal 201'. Light 213 is also phase shifted by 90 degrees relative to light 205' by phase shifter 224. The phase shift between 205' and 213 will help prevent cross talk between the fluorescence that is ultimately excited by this light.

Light 205' is directed to beam splitter 226A. Portion 205A of light 205 is directed to photodetector 228A, which generates corresponding electrical signal 207'. Electrical signal 207' is directed to signal processing system 110 and is used as a measure of the intensity of the excitation light during signal processing. Similarly, light 213 is directed to beam splitter 226B. Portion 213A of light 213 is directed to photodetector 228B, which generates corresponding electrical signal 215. Electrical signal 215 is directed to signal processing system 110 and is used as a measure of the intensity of the excitation light during signal processing.

Portion 205B' from beam splitter 226A and portion 213B from beam splitter 226B are directed to beam splitter 230. This beam splitter is designed so that it is nearly fully transmissive to light 205B' and nearly fully reflective to light 213B. The light exiting beamsplitter 230 is directed to excitation-light delivery/signal recovery optics 104. This light will ultimately illuminate the region of interest in test subject 101.

Figure 8:
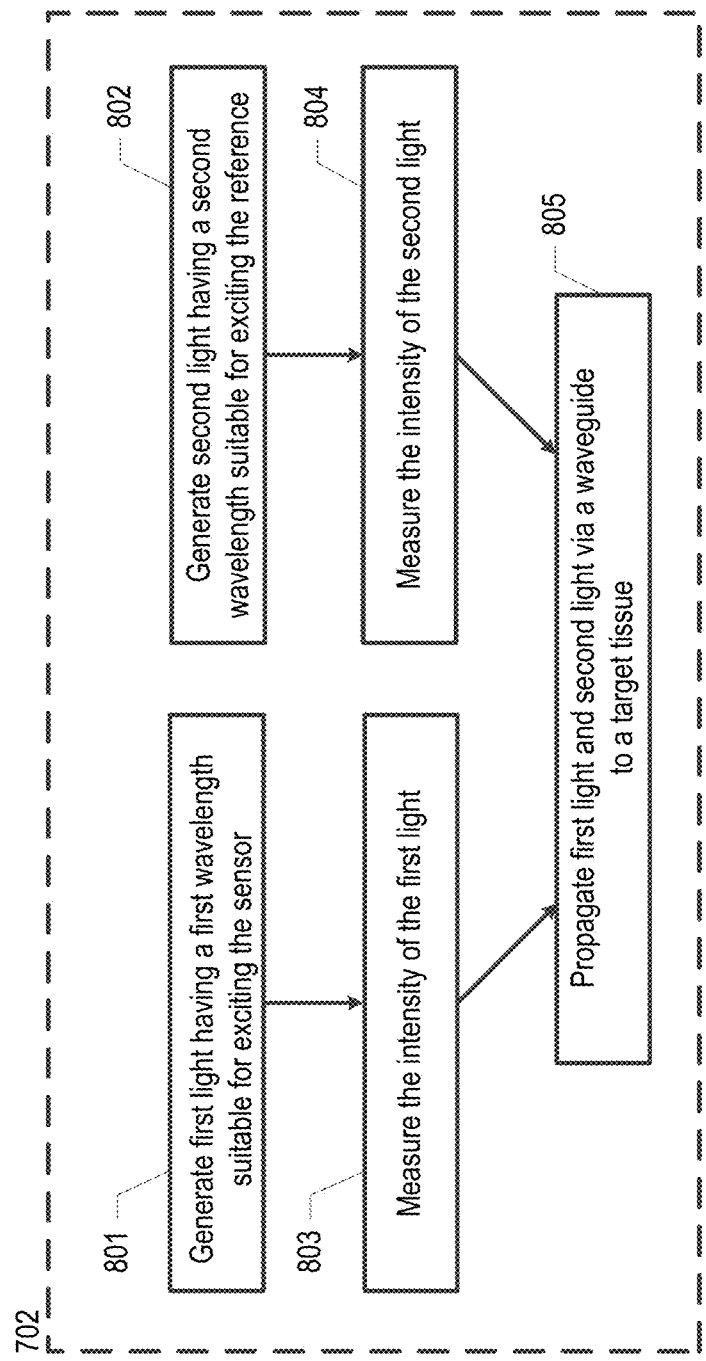
FIG. 8 depicts tasks for implementing step 702 of the method of FIG. 7

Returning to the discussion of method 700, and in particular step 702 thereof ("deliver excitation light to target tissue"), in accordance with an illustrative embodiment and with reference to FIG. 8, step 702 further includes tasks 801 through 804. Per task 801, light having a first wavelength suitable for exciting the sensor is generated. Per task 802, light having a second wavelength suitable for exciting the reference is generated. If optical measurement/recording system 100 includes a single light source (e.g., per the embodiment of FIG. 2A), then the light generated therefrom will include wavelengths suitable for exciting both the sensor and the reference. If system 100 includes two sources (e.g., per the embodiment of FIG. 2B), then one of the sources will generate the light having (as its center or most predominant wavelength in terms of intensity) the first wavelength and the other of the sources will generate the light having (as its center or most predominant wavelength in terms of intensity) the second wavelength.

Figure 9A:
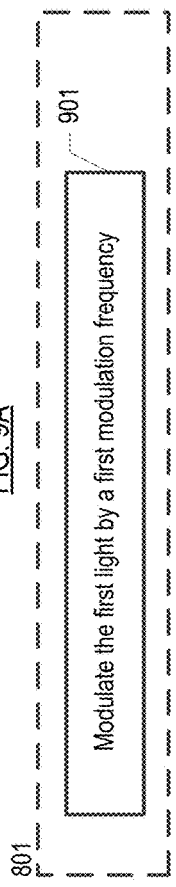
FIG. 9A depicts a sub-task for implementing one of the tasks shown in FIG. 8.
Figure 9B:
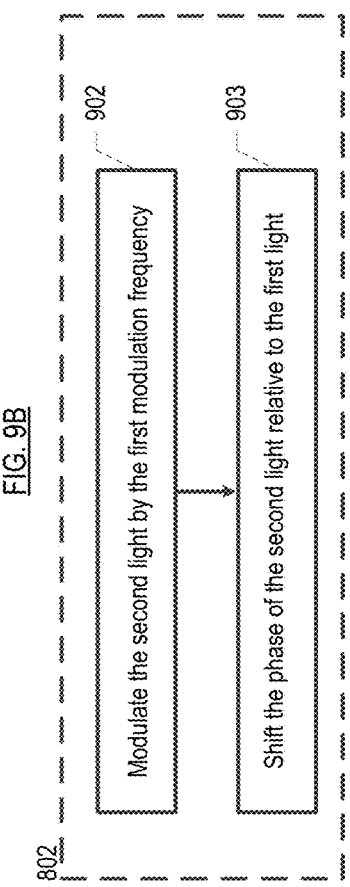
FIG. 9B depicts sub-tasks for implementing one of the tasks shown in FIG. 8.

As depicted in FIG. 9A, task 801 includes sub-task 901, wherein the first light is modulated by a first modulation frequency, as discussed above in conjunction with FIGS. 2A and 2B. As depicted in FIG. 9B, task 802 includes sub-task 902, wherein the second light is modulated by the first modulation frequency and sub-task 903 wherein the second light is phase shifted (e.g., by 90 degrees, etc.) relative to the first light.

Returning to the discussion of FIG. 8, in accordance with tasks 803 and 804 of step 702, the intensity of the first light and the intensity of the second light is measured. This is particularly advantageous when two light sources are being used, because the noise generated by the two light sources is unlikely to be correlated. As discussed further below, the intensity measurements are used in conjunction with the signal processing of step 704 of method 700.

In task 805, at least some of the intensity of first and second light generated in tasks 801 and 802 is propagated, via a waveguide, to the target tissue. As depicted in FIG. 3, in the illustrative embodiment, the waveguide are two optical fibers (i.e., fibers 334 and 338).

FIG. 3 depicts further details of an embodiment of excitation-light delivery/signal recovery optics 104, signal color separation 106, optical-to-electrical conversion 108, and signal processing subsystem 110.

In the illustrative embodiment, subsystem 104 comprises free-space and as well as guided optics, including dichroic beam splitter 330, lens 332, optical fiber 334, and fiber optic ferrule 336, and optical fiber 338.

In accordance with this embodiment, the light from excitation-light subsystem 102 (either 205B or 205B'/213B) is directed to dichroic beam splitter 330. This light passes through the beam splitter 330 and enters lens 332. The lens collimates and focuses excitation light 321 into optical fiber 334. In the illustrative embodiment, optic fiber 334 is multi-mode and the core diameter is matched to that of the excitation light.

Excitation light 321 is propagated along optical fiber 334 to fiber optical ferrule 336, which is coupled to the test subject. Optical fiber 338 extends from the ferrule into test subject 101. In the illustrative embodiment, optical fiber 338 extends in to region of interest 462 in brain 460 of test subject 101, as depicted in FIG. 4.

Figure 4:
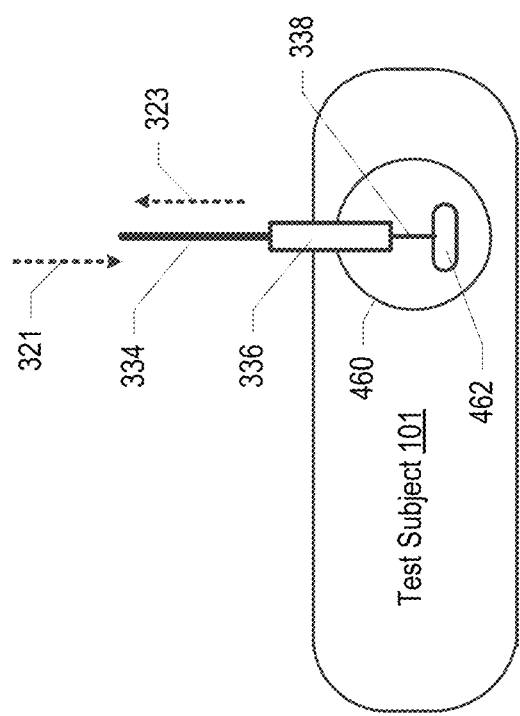
FIG. 4 depicts the optical measurement/recording system of FIG. 1 used in conjunction with a test subject.

Referring now to FIG. 4, and with continuing reference to FIG. 3, in the illustrative embodiment, excitation light 321 stimulates fluorescence (hereinafter "signal") 323 in the sensor(s) and reference(s) (not depicted) in the region of interest. As previously indicated, in the illustrative embodiment, the fluorescence contains information pertaining to biological parameter in the region of interest as well as physiological and other artifacts. Fluorescence 323 (or other optical response in other embodiments) enters fiber 338 and is coupled to and propagated along optical fiber 334 to dichroic beam splitter 330. The splitter is designed so that the wavelengths of the fluorescence that is emitted by the sensor(s) and reference(s) is within a range of wavelengths that are reflected by the splitter.

Fluorescence is thus directed toward signal color separation 106, which in the illustrative embodiment is implemented as beam splitter 340. Beam splitter separates the fluorescence into two optical signals (colors) 323A and 323B, which, in the illustrative embodiment, are: (i) green light generated by the sensor and containing information pertaining to membrane voltage and artifacts, and (ii) red light generated by the reference and containing information pertaining to the artifacts but not membrane voltage.

Optical signal 323A and 323B are directed to optical-to-electrical conversion 108, which in the illustrative embodiment is implemented as photodetectors 342 and 344. Photodetector 342 converts optical signal 323A into a corresponding electrical domain signal 325 and photodetector 344 converts optical signal 323A into a corresponding electrical domain signal 327. Electrical signals 325 and 327 are then transmitted to signal processing subsystem 110.

Figure 10:
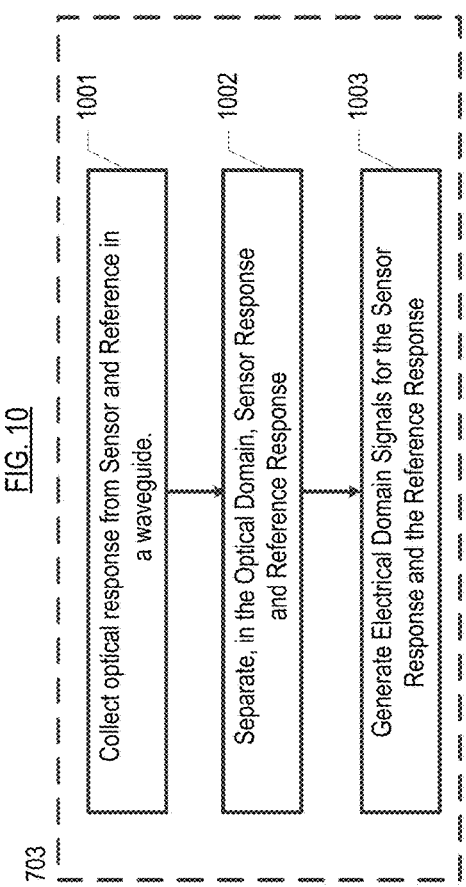
FIG. 10 depicts tasks for implementing step 703 of the method of FIG. 7.

FIG. 10, which depicts sub-tasks of step 703 "collect optical domain sensor response and reference response," recites at least some of the functionality of sub-systems 104, 106 and 108. In particular, sub-task 1001 recites, collecting the sensor and reference response in a waveguide, which, in the illustrative embodiment, is the same waveguide that delivered excitation light to the target tissue. In sub-task 1002, the sensor response and the reference response are separated (in the illustrative embodiment by wavelength), in the optical domain. And in sub-task 1003, the separated optical signals are converted to electrical-domain signals.

In the illustrative embodiment, signal processing subsystem 110 includes preamplifier 346, lock-in amplifiers 348, and processor 350, and processor accessible storage 352. These devices, as well as their function, are well known to those skilled in the art. Briefly, preamplifier 346 contains circuitry for amplifying electrical signals and lock-in amplifiers 348 are used for generating a modulation signal (i.e., 201 or 201') and extracting a signal with a known carrier wave from very noisy environments. Processor 350 is a general-purpose processor that is capable of executing software that implements artifact separation algorithm 354. In some alternative embodiments of the present invention, processor 350 is a special-purpose processor. Processor-accessible storage 352 is a non-volatile, non-transitory memory technology (e.g., hard drive(s), flash drive(s), etc.) that stores the code for artifact separation algorithm 354, in addition to any other software.

In operation, signals 325 and 327 and signal 207 (FIG. 2A) or signals 207' and 215 (FIG. 2B) are amplified by pre-amplifier 346. The signals are demodulated by lock-in amplifiers 348, one lock-in amplifier for each of the signals. The signals are then processed in processor 350 in accordance with artifact separation algorithm 354. The output of signal processing subsystem 110 includes a signal representative of the biological parameter of interest (e.g., a neural signal, etc.), free of artifacts and one or more signals that contains information pertaining to the artifacts. The artifact separation algorithm is discussed in further detail in conjunction with FIGS. 5A and 5B.

Figure 5A:
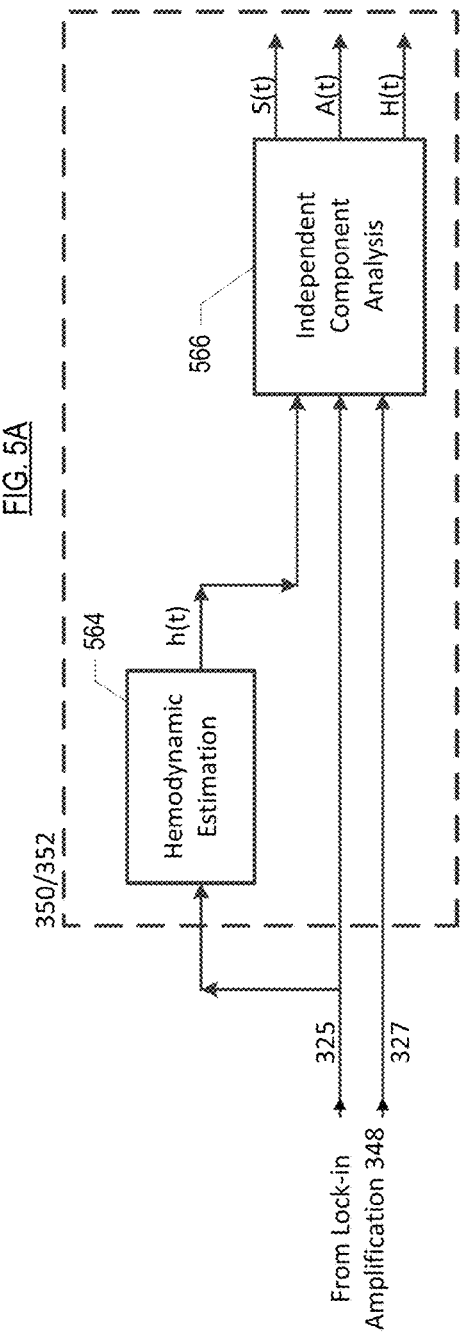
FIG. 5A depicts a first embodiment of the artifact separation process used in the signal processing subsystem of the optical measurement/recording system of FIG. 1.
Figure 5B:
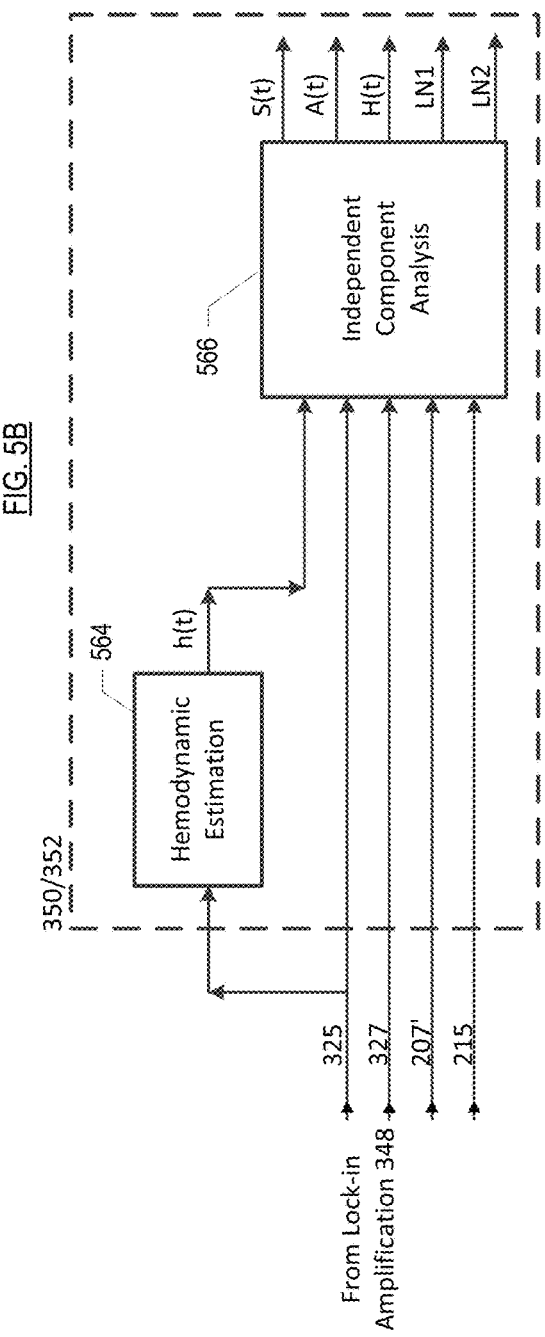
FIG. 5B depicts a second embodiment of the artifact separation process used in the signal processing subsystem of the optical measurement/recording system of FIG. 1.

FIG. 5A depicts an embodiment of artifact separation for a scenario in which optical measurement and recording system 100 includes excitation-light subsystem 102-1 including a single light source. FIG. 5B depicts an embodiment of artifact separation for a scenario in which optical measurement and recording system 100 includes excitation-light subsystem 102-2 including two light sources.

The inventors designed the artifact separation as a two-stage process, wherein in the first stage, a mathematical model of (ongoing) hemodynamic noise sources is developed from measurements in the reference channel. In the second stage, independent component analysis (ICA) is applied to determine a linear un-mixing matrix for sorting the biological signals of interest (in the illustrative embodiment—trans-membrane voltage signals) and physiological artifacts into separate time traces. That is, ICA 566 is used to "un-mix" the (electrical domain analogues) of the fluorescence signals into statistically independent components (membrane voltage and various artifacts) and identify their relative contributions to the fluorescence signals.

As depicted in FIG. 5A, inputs to ICA 566 include signals 325, 327, h(t). One of the signals 325 or 327 is based on fluorescence predominantly from the fluorescent protein that is non-sensitive to the biological parameter of interest (e.g., membrane voltage). That signal contains hemodynamic artifacts and other artifacts (e.g., movement related, etc.), and includes laser noise that is common to both signals 325 and 327 (since there is a single source in excitation-light subsystem 102-1). The other of the signals 327 or 325 is based on fluorescence predominantly from the fluorescent protein that is sensitive to the biological process of interest. This signal is also contaminated with hemodynamic artifacts and other artifacts and includes the common laser noise.

As depicted in FIG. 5B, inputs to ICA 566 include signals 325, 327, h(t), 207', and 215. Signals 207' and 215 provide the intensity of the two excitation light sources. The inclusion of signals 207' and 215 is important because signals 325 and 327 are contaminated by noise from light sources 220A and 220B that is not common for the two color channels.

The signal h(t), which is an estimate of hemodynamic artifacts present in signals 325 and 327, is generated by hemodynamic estimation process 564, which is discussed further below.

For the embodiment of the artifact separation process depicted in FIG. 5A, the outputs of ICA 566 are the following "unmixed" or pure signals: neural signal S(t), motion artifacts signal A(t), and hemodynamic artifacts signal H(t). For the embodiment of the artifact separation process depicted in FIG. 5B, the outputs of ICA 566 are the following unmixed signals: neural signal S(t), motion artifacts signal A(t), hemodynamic artifacts signal H(t), noise signal LN1 from light source 220A, and noise signal LN2 from light source 220B.

Returning again to method 700, step 704 recites extracting a signal representative of a biological parameter of interest. As discussed above, and as depicted in FIG. 11, this step includes tasks 1101 and 1102. Task 1101 involves generating an estimate of hemodynamic artifacts present in the sensor response from information contained in the reference response. Per task 1102, a linear un-mixing matrix is generated for sorting the biological signals of interest from the physiological artifacts. Furthermore, per FIG. 12, task 1102 comprises the subtask of receiving, at a processor, electrical domain signals representative of sensor response, reference response, an estimate of hemodynamic artifacts, and excitation-light intensity (when two separate light sources are used).

For the following discussion of the artifact removal process, signal 325 is assumed to be the electrical-domain analogue of the observed red fluorescence, r(t) and signal 327 is assumed to be the electrical-domain analogue of the observed green fluorescence, g(t). Signal 207' is assumed to be the electrical-domain light intensity signal from a red light source and signal 215 is assumed to be the electrical-domain light intensity signal from a green light source. Signals g(t) and r(t) are products of contributions from relative changes in observed fluorescence arising from neural signals, S(t), motion artifacts, A(t), hemodynamic artifacts, H(t), fluctuations in the laser's mean power, L(t), and fluctuations due to photon shot noise and the photodetector's electronic noise in the two emission channels (approximated as stationary Gaussian distributions with standard deviations $\sigma_r$ and $\sigma_g$):

$$g(t)=g_0[1+S(t)+A(t)+H(t)]\cdot[1+\alpha L(t)]\mathcal{N}(0,\sigma_g) \quad [1]$$

$$r(t)=r_0[1+\delta S(t)+\lambda_1 A(t)+\lambda_2 H(t)]\cdot[1+\alpha L(t)]+\mathcal{N}(0,\sigma_r) \quad [2]$$

where:
- $g_0$ and $r_0$ are the mean fluorescence intensity of each color channel,
- $\delta$ models the extent of the crosstalk between the two channels,
- $\lambda_1$ and $\lambda_2$ equal the ratio of the magnitudes of the physiological artifacts in the two channels, and
- $\alpha$ accounts for differences in the magnitude of the non-stationary fluctuations observed in the direct measurements of laser power and those resulting in the fluorescence traces.

These parameters can vary widely depending on the individual preparation and the relative intensity of the two fluorescence channels. For example, in sample trials, $\delta$ ranged between 0.001-0.1, depending on the relative emission power in the two channels. And $\lambda_1, \lambda_2$ were between 0.2-2 due to differences in fluorescence baseline between the two channels and spectral differences in hemoglobin absorbance. Parameter $\alpha$ was generally between 0.2-1 due to differences in photodiode filter properties, lock-in amplifier settings, and possible differences in the spatial distribution of laser fluctuations between the photodiode and optical fiber.

The variances of these fluctuations are small compared to unity: Var[S(t)], Var[L(t)], Var[A(t)], Var[H(t)]~0.01. The products of the perturbations can therefore be ignored such that expressions [1] and [2] can be written as:

$$g(t)=g_0[1+S(t)+A(t)+H(t)+\alpha L(t)]+\mathcal{N}(0,\sigma_g) \quad [3]$$

$$r(t)=r_0[1+\delta S(t)+\lambda_1 A(t)+\lambda_2 H(t)+\alpha L(t)]+\mathcal{N}(0,\sigma_r) \quad [4]$$

Independent component analysis applied to g(t) and r(t) determines a weight vector W that maximizes the non-Gaussianity of the projected fluorescence traces. This will produce statistically independent sources:

$$c_1(t)=W_{11}g(t)+W_{12}r(t) \quad [5]$$

$$c_2(t)=W_{21}g(t)+W_{22}r(t) \quad [6]$$

The fluctuations S(t), A(t), H(t) and L(t) are non-Gaussian, and are expected to be statistically independent. Therefore, in the noise-free case, with $\lambda_1=\lambda_2=1$, ICA is guaranteed to recover sources of the form $c_1(t) \propto S(t)$; $c_2(t) \propto A(t)+H(t)+\alpha L(t)$, as sources that mix S(t) and physiological artifacts will not be statistically independent.

Initial attempts at artifact removal used ICA alone, since recordings in mice expressing the control fluorophores YFP and mCherry showed strong correlations between the green and red fluorescence channels, suggesting equal contributions in each channel from motion and hemodynamic noise sources. Although ICA alone was effective in some mice for removing both motion and blood-flow artifacts, in other mice some hemodynamic components remained in the un-mixed signal channel, likely due to unequal scaling of the two artifacts between the color channels.

Most ICA algorithms are unsuited for undetermined problems in which the number of sources is greater than the number of signals, preventing extraction of more than two sources from the traces in the illustrative embodiments. Numerous extensions of ICA exist that enable un-mixing of more sources than signals, typically by projecting recorded signals into a large basis set, such as the Fourier or wavelet basis, in which the sources are thought to be sparse. In embodiments of the present invention, however, the signals contain both broadband motion artifacts and narrowband hemodynamic artifacts, and a relatively high amount of photon shot noise, preventing a straightforward application of most undetermined algorithms.

The inventors recognized that by directly estimating the narrowband hemodynamic source from the reference trace, it could be used as a separate input into ICA. The hemodynamic noise source was modeled as a sinusoid with time-varying amplitude, phase, and frequency:

$$h(t)=a(t)\sin[2\pi f(t)+\phi(t)] \quad [7]$$

Advantageously, this model could be extended to incorporate the harmonics of hemodynamic noise at integer multiples of the heartbeat frequency. The various parameters were estimated from the red fluorescence trace by dividing the trace in two-second bins and performing a least-squares curve fit between r(t) and h(t) in each bin. The signals h(t), r(t), and g(t) were then simultaneously unmixed with ICA as above, and denoted the signal source as:

$$c_1(t)=W_{11}g(t)+W_{12}r(t)+W_{13}r(t) \quad [8]$$

chosen as the trace with the largest relative contribution from the green fluorescence channel. To preserve the shot-noise statistics and the size of fluorescence changes in the un-mixed sources, the rows of the mixing matrix W were normalized such that:

$$W_{11}=W_{22}=W_{33}=1 \quad [9]$$

In cases when expression of the red reference fluor was dim, both laser light sources are used. The amplitudes of the two lasers were modulated 90 degrees out of phase and their emission powers were continuously monitored, $P_g(t)$ and $P_r(t)$, respectively. Ignoring the products of perturbations as above, and dividing each optical signal by its mean intensity, the following relations are obtained:

$$g'(t)=1+S(t)+A(t)+\alpha_g L_g(t)+\mathcal{N}(0,\sigma'_g) \quad [10]$$

$$r'(t)=1+A(t)+\alpha_r L_r(t)+\mathcal{N}(0,\sigma_r') \quad [11]$$

$$P_g'(t)=1+L_g(t) \quad [12]$$

$$P_r'(t)=1+L_r(t) \quad [13]$$

The prime index denotes the signals normalized by their mean intensity (e.g. $g'(t)=g(t)/g_0$). Linear scaling of laser power fluctuations is accounted for by the constants $\alpha_g$ and $\alpha_r$, to reflect possible differences in photodiode filter properties, lock-in amplifier settings, and the mode characteristics of laser fluctuations.

Using ICA allows for an un-mixing as above, with the resultant signal vector $$c_1'(t)=W_{11}g'(t)+W_{12}r'(t)+W_{13}P_g'(t)+W_{14}P_r'(t) \quad [14]$$

It is notable that because the un-mixing procedure is additive, the un-mixed signals contain photon "shot noise" contributions from both the signal and reference channels. As a consequence, it is important to minimize shot noise present in the reference channel by increased expression density of red fluors. It was found that using bright fluors that were widely expressed in the brain, such as transgenically expressed tdTomato, provided the highest optical intensity and thus the lowest added shot noise to the un-mixed signals.

APPENDIX I, which follows below, provides a protocol, consistent with the foregoing disclosure and the illustrative embodiment, for performing cell-type specific monitoring of transmembrane voltage in freely moving mice.

It is to be understood that the disclosure teaches just one example of the illustrative embodiment and that many variations of the invention can easily be devised by those skilled in the art after reading this disclosure and that the scope of the present invention is to be determined by the following claims.

APPENDIX 1

This is a protocol for performing cell-type specific monitoring of transmembrane voltage in freely moving mice. This measurement is performed optically, and therefore we call it 'Transmembrane Electrical Measurements Performed Optically' (TEMPO). To optically resolve neural voltage during behavior, TEMPO combines two-color, highly-sensitive fiber optic instrumentation, with genetically encoded voltage sensors that have been virally delivered to specified cell populations.

Many voltage sensors exist and are suitable for use with TEMPO, and should be selected based on the sensors d', a holistic measure that incorporates the brightness, speed, and dynamic range of the sensors. The existing sensors with the largest d' are MacQ-mCitrine, ASAP1, and the Arclight variants, of which MacQ-mCitrine has received the most testing using TEMPO.

Many techniques exist for optically recording neural activity in vivo using fluorescent sensors of intracellular calcium or transmembrane voltage. These include one- and two-photon microscopy techniques capable of recording activity in superficial brain regions, and approaches using implanted endoscopic lenses that allow optical access to deep brain regions. Most of these techniques are only suited to monitoring changes in intracellular calcium. Calcium dynamics correlate with neuronal activity, but are ~200-fold slower than voltage dynamics and can be optically reported with large dynamic range by existing genetically encoded sensors (~10-30% for a single action potential).

While specialized systems exist for monitoring changes in intracellular voltage in culture, no standard approach exists for optically recording voltage in single cells in vivo. Multiple imaging methodologies have been developed to optically record intracellular voltage from populations of cells in vivo using voltage-sensitive dyes. However none of these systems are capable of recording from deep brain regions, and few are none capable of correcting for motion-artifacts, as most are designed for anesthetized imaging experiments.

TEMPO uses two-color fiber optic instrumentation, genetically-encoded voltage sensors, and an optical reference channel to recording the aggregate voltage dynamics of genetically-specified cells throughout the deep brain. While fiber optics have long been used for neural recordings, TEMPO's design allows a 10-fold improvement in sensitivity over previous techniques.

The protocol for performing TEMPO can be divided into four stages: (1) construction of the TEMPO implant, (2) intra-vital surgery for the viral labeling of cells and implanting the TEMPO probe, (3) construction of the TEMPO instrument, and (4) TEMPO experiments recording activity in freely moving animals. The TEMPO probe is similar to an optrode, and multiple protocols for optrode construction and implantation. As a result, a more cursory description of these steps is provided, keeping the focus on the construction of the TEMPO instrument and the performance of TEMPO experiments.

Step #1: Implant Manufacturing
Implant Materials.
Implant Workstation
Stereomicroscope (e.g. Leica MZ7-5)

Vice for holding small elements (Panavise 301, Base Panavise 312)
Helping hands (TEKTON 7521)
Heat gun (Kester HG-300D)
Solder station, mat, cleaner (e.g. Weller PES51, WESD51, Hakko 599B-02)
Surgical Scissors for cutting wire (FST 14084-08)
Hemostat for holding implanted fibers (Fisher F899-84)
Fine forceps for stripping wire (Techni-tool 758TW0304)
Wire cutters and pliers (Xcelite S2K)
Implant Consumables
Solder (McMaster 7758A1)
Neuralynx interface boards and headstages (Neuralynx EIB8, HS-8-CNR-MDR50)
Cyanoacrylate (Great Planes GPMR6007)
Coated stainless steel wire (0.005" bare, 0.008" coated, 100 feet, A-M systems 91400)
Tungsten wire (California Fine Wire 0.002" M215580, 1000 feet)
Skull screws (Component Supply Co, MX-000120-01SFL, #000 Machine Screws)
2.5 mm Fiber optic implants (400 um 0.39 NA, Thorlabs CFM14L05-CFM14L10)
Polymidide tubing (24 AWG, 0.0201 ID, 0.0030 Wall, 30 inches; Smallparts TWPT-0201-30)
Post-it notes (Post-it 654-5SSY)
Gold pins (Neuraynx, Small EIB Pins)
Weigh boats for glue and holding materials (Santa Cruz sc-201606)
Wire for applying glue
Manufacturing Instructions.
Make Skull Screws for EEG.

First trim stainless steel wire to ~1.5" in length, then strip coating from last ~2 mm of either end using fine forceps. Wrap steel wire around the base of the screw several times to hold in place. Place base of skull screw in helping hands clamp. Apply a drop of solder flux to the base of the bare end of the steel wire and the screw base using a wire applicator. Solder the steel wire in place on the base of the screw, taking care not to apply solder to the groove of the skull screw threads.

Manufacture the Twisted Pairs of Tungsten Wires Used for the EMG and LFP.

Cut 2-3" pieces of tungsten wire, grasp both ends evenly and place them in the vice. Tighten the vice so that both ends are firmly held. Insert a small q-tip end or steel rod inside the loop that is formed, and twist until the wire is twisted along the full length. Briefly apply heat using a heat gun to melt the insulation of the two sides to one another and preserve the twisting after removal from the vice. Use scissors to cut the remaining loop in the wire. For LFP wires, cut ends to be even with one another. For EMG wires, leave ~5 mm between the wire tips.

Attach LFP Wires to the Optical Fiber.

Cut a ~2 mm long piece of polyimide tubing. Place it on the sticky end of a post-it note to hold it in place. Thread a twisted pair of tungsten wires through the tube, and insert an optical fiber ferrule implant alongside. They should fit snugly. Adjust the position of the wire so that it is at the fiber tip. Place a small amount of cyanoacrylate glue in a weigh boat, and use a wire applicator to apply a droplet to the rear of the polyimide tube to secure the wire in place. Let dry.

Solder EEG Wires to the Interface Board.

First map out the desired input and output of the interface board on paper. Hold the interface board in helping hands with the underside facing up. Insert the bare end of the EEG wires through the board and bend the tip of the bare end so that the wire end doesn't fall out. Apply a drop of flux to each wire end, and solder the wire to the interface board.

Insert LFP and EMG Wires into the Interface Board.

Take the two longest ends of the twisted pairs of tungsten wires, and insert each end through the desired position in the interface board. Bend the ends with forceps to hold them in place. Grasp gold pins with pliers and place through each hole. Use pliers to secure gold pins in place. The pins should shear the insulation along the wire to make electrical contact with the interface board. The optical fiber attached to the end of the LFP wires should be hanging off the board.

Attach the Optical Fiber to the Interface Board.

Use a second helping hands clamp to bring the optical fiber into contact with the board. Apply UV glue to the board and ferrule of the fiber implant to secure it in place.

Coat the Bottom of the Implant with Dental Acrylic.

Ensure that the top of the interface board is in the helping hands, with the underside flat facing upwards. Mix a small amount of dental acrylic in a weigh boat and apply it to the underside, covering the base of the board. Wait 15 minutes before implantation.

Step #2: Mouse Surgery
Surgery Reagents
Voltage sensor viruses or plasmids: MacQ-mCitrine (Addgene, Plasmid #48762), ASAP1 (Addgene, Plasmid 52519), ArclightQ239 (Addgene, Plasmid 36855; University of Pennsylvania Vector Core, AV-1-36857P)
Control and reference fluorophore Viruses: (University of North Carolina Vector Core, AAV-CaMKIIa-EYFP, AAV-CaMKIIa-mCherry)
Surgery reagents (Saline, PBS, Water, Betadine, 70% ethanol, Q-tips, bleach, weigh boats, surgical mats)
Surgical drill (Osada EXL-M40, Osada L12M)
Fine drill bits (FST 1900705)
Stereotactic frame (Kopf 900)
Heating pad (FHC 40-90-2-07)
Temperature controller for heating pad (FHC 40-90-8D)
UV curable glue (Loctite 4305, 74545A52, McMaster)
Stereoscope (Leica Wild M3Z)
Light source for stereoscope (Schott-fostec A20500, Schott-fostec A21200)
Syringe pump (WPI UMP3-1)
Injection syringe (WPI NANOFIL-10 ul)
Isoflurane anesthesia system (Vetequip, 901806)
Metabond (Parkell, S380)
Dental resin (Coltene H00357)
Vetbond (Santa Cruz Biotechnology, sc-361931)
Stereotax tool holder (Kopf 1766-AP Cannula)
Aluminum Headbars (Custom)
Sutures (Harvard 510479)
Nair (Fisher NC0117021)
Eye lubricant (Henry Schein 4725942)
Hemostat with scissors for cutting sutures (FST 12002-12)
Brain holder for histology (FST 10099-15)
Fine Forceps (FST 11254-20 or similar)
Surgical scissors (FST 14084-08)
Screwdriver for inserting skull screws (FST 30051-10)
Blunt forceps (FST 11223-20)
Surgery Instructions.
Perform Craniotomy Above Structure of Interest.

Remove hair from scalp using Nair. Remove the skin overlying the cortex, let the skull dry, and drill above the structure of interest.

Locate the Coordinates of Structure of Interest in a Brain Atlas.

Inject Virus. Inject 500 nl of each virus at 100 nl/min, leave in place for 10 minutes, withdraw.

Suture Scalp.

Ensure Viral Expression Histologically.

Re-Open Skull.

Two weeks after viral injection, reopen the scalp, perform a second craniotomy and re-open the skull over the region.

Drill Holes for Skull Screws.

Drill three holes in the frontal, parietal and cerebellum for skull screws.

Aspirate.

Lightly aspirate above the structure to prevent tissue compaction.

Implant Fiber Optic Ferrule.

Place plastic sheath around fiber optic ferrule and place inside a cannula holder above the injection site.

Screw in Skull Screws.

Before implanting fiber, screw in skull screws. Then zero the tip of the fiber optic ferrule at Bregma and implant to the desired coordinates. Use UV glue to seal. The fiber in place, and headbar.

Apply Metabond.

Apply a thin layer of Metabond and wait for 5 minutes. Follow by applying a thin layer of dental cement.

Wait.

Wait several weeks before recording as fluorescence will improve.

Step #3: Build, and Test the Optical Setup

Optical Instrumentation.

Obis 561 and 488 Lasers (OBIS 481 and 561 LS, Coherent, fiber coupled to FC/PC, with heatsink)

Fiber optic patch-cord (Thorlabs 400 EMT 0.39 NA, 2 meters, stripped bare, FC/PC and ferrule connectorized)

Motorized Shutter (Thorlabs SC10 and SH1)

2× Variable gain photoreceiver (OE 200 SI, Femto, free-space coupled)

2× Photodiodes (Thorlabs PDA 100 A)

Optical elements:
  2× 50-50 Beamsplitters (Thorlabs CM1-BS013)
  2× 30 mm Neutral density filters (Thorlabs NE505B, NE510B, NE503B, NE520B placed in a CFW6 wheel)
  1× Dichroic for combining lasers (Semrock FF511-Di01)
  1× Dual-band excitation dichroic (Semrock FF493/574-Di01)
  1× Collection filter set (Semrock FF564-Di01, FF01-630/92, FF01-537/26)
  4× Aspheric lenses for fiber coupling (Thorlabs A240TM)

Optomechanics:
  2× 5-axis fiber coupler and cage plate (Thorlabs PAF-X-7A, CP08FP/M)
  30 mm Cage rods (Thorlabs ER05, ER1, ER025, ER15, ER2)
  30 mm Cage plates (Thorlabs CP02, CP02-T)
  1" Lens tubes (Thorlabs SM1L05, SM1L10)
  4× X-Y positioners (2× Thorlabs CXY1 and 2× QIOPTIQ G061025000)
  3× Removable filter cube (Thorlabs DFM)
  ½" Optical posts (Thorlabs CF175, PH2, BE1, TR2 or similar)
  An optical breadboard (Thorlabs MB1218 or similar)
  FC/PC fiber cage adapter (Thorlabs SM1FCA)
  Cage cube connectors (Thorlabs CM1-CC)

Electrical Instrumentation.
  4× Lock-in amplifiers (SRS 810, 830 or 850 or other)
  Electrophysiology (Neuralynx, Lynx-8 amplifier with ERP-27)
  All pass filter (Custom built)
  A/D card (National instruments NI PCIe-6320, SHC68-68-EPM, BNC-2090A)
  Custom analysis software (Matlab, sample provided)
  Behavior camera (AVT Guppy Pro F-125 ⅓" CCD Monochrome Camera #68-567)
  18" Rackmount (Startech 42U)

Instrumentation Setup.

Construct the Input Excitation Pathway.

Support all large elements on optical posts, secured with clamping forks. Couple the fiber pigtailed lasers to the 5-axis coupler For each excitation arm, attach the 5-axis coupler to a cage plate, attach the cage plate to the beamsplitter using cage rods. Use a lens tube to couple the photodiodes to the beamsplitter. Attach the beamsplitter cubes to the neutral density filter wheels using cage rods. To combine the beams, attach the neutral density filter wheels to the filter cube containing a (FF511-Di01) dichroic with cage rods. Ensure proper orientation of the two input pathways in the dichroic. Using cage rods and a double-sided cage plate, attach the combined beams to the motorized shutter. Use lab tape to secure the input fiber to the instrument to reduce vibration. Use cable ties, screws and lab tape to reduce any strain on the electrical cables.

Construct the Collection Pathway.

Attach the second side of the motorized shutter to a filter cube, containing a dual-band dichroic (FF493/574-Di01). Attach a cage plate to the output of the cube. Insert a mounted aspheric lens into the cage plate, and focus this onto the FC/PC coupled output fiber. Use a cage plate coupler to attach a last filter cube to the opposite side of the excitation cube. Attach the other two aspherics to the output arms of the filter cubes using cage rods. Attach the photoreceivers to the QIOPTIQ x-y positioners and into the output path. Make sure to use cable ties, screws and tape to reduce any strain on the cables that could add torque to the system.

Setup the Data Acquisition.

Use one lock-in amplifier to amplitude modulate the lasers at a chosen frequency. Use an all-pass filter to shift the 561 nm laser by 90 degrees. Use two lock-in amplifiers to lock-in the photodiode measurements of laser power. Use the other two amplifiers to lock-in the photoreceivers. Attach the lock-in output to BNC breakoutboard of the National Instruments acquisition system.

Align the Output Fiber to the Photorecievers.

Attach one of the input lasers to the output FC/PC port and coarsely align the laser to the output photoreceivers by removing the filter cube inputs. Use X-Y translation stages attached to the photorecievers to fine-tune the alignment of the output, adjusting the X-Y position of the output fiber if necessary.

Align the Input Lasers to the Output Fiber to Minimize Autofluorescence and Maximize Power.

Ensure that the two excitation lasers are coarsely aligned into the output fiber. After setup, attach fiber optic patch cord to the system's FC/PC output, and illuminate a power meter with the other end. Turn on one excitation source. Simultaneously record the power output of the patch cord and the autofluorescence generated by the patch cord cladding in the photorecievers. Fine tune the alignment of the excitation source by adjusting the five-axis mount. Optimize the power output from the patch cord while minimizing the autofluorescence recorded at the photoreciever. Repeat with the second excitation source.

Assess and Reduce the Optical Noise Due to Shot-Noise, Laser Noise and Vibrations.

Using helping hands or another tool, bring the tip of the output fiber in close and stable proximity to a fluorescent slide, lab tape, or a highlighter pen. Record the sample fluorescence for several minutes. Compute the power spectral density of the observed fluorescence, and compare it to the computed electrical read noise and photon shot noise calculated from the properties of the detector and light intensity. The two spectra should be closely matched, aside from stray peaks due to laser noise and low frequency drift.

Troubleshooting if Excess Low-Frequency Noise.

Ensure excitation fibers are taped down. Ensure output fiber and illuminated object are securely held.

Step #4: Use TEMPO in Control and Biological Experiments

Assess Noise in a Live Animal Expressing Control Fluorophores.

Implant fiber probe above YFP and mCherry expression as in the surgery section. Record fluorescence and electrical activity near the fiber probe under three conditions: under isoflurane anesthesia, under ketamine-xylazine anesthesia and while animals are freely moving. Under isoflurane anesthesia there should be little electrical activity, but prominent 5-15 Hz heartbeat artifacts and possibly breathing artifacts (0.3-2 Hz). Under ketamine-xylazine anesthesia, there should be low-frequency electrical oscillations and prominent heartbeat artifacts uncorrelated with the oscillations. In freely moving conditions there should be some electrical activity and large artifacts due to movement and heartbeat.

Troubleshooting if No Heartbeat Artifact is Observed.

First make sure you are recording fluorescence from the brain, and not autofluorescence from the implanted ferrule. Make sure the fluorescence recorded from the brain is higher than that recorded from the implant, preferably 2-10 fold higher. If little fluorescence is observed, raise the power used, raise the amplifier gain, or check histology to ensure viral expression is present. Verify expression histologically.

Record from an Animal Expressing a Voltage Sensors and a Reference Channel.

Implant fiber probe above the region where the voltage sensor and reference are expressed. Record from animals under three conditions: isoflurane anesthesia, ketamine-xylazine anesthesia and while animals are freely moving. Under isoflurane anesthesia there should be little electrical activity, but prominent heartbeat artifacts in both the voltage sensor and reference channel. Under ketamine-xylazine anesthesia, there should be low-frequency oscillations and prominent heartbeat artifacts uncorrelated with the oscillations. In freely moving conditions there should be some electrical activity and large artifacts due to movement and heartbeat.

Troubleshooting: Fluorescence, but not Neural Signals are Observed.

First make sure electrical activity is observed under ketamine-xylazine anesthesia to ensure signals are present. Next, look at the amplitude of noise in the traces. Optical signals are small (~1-2%), and can buried in shot-noise or other noise sources. Turn up the power briefly to see if shot-noise is limiting detection of neural signals.

Data Un-Mixing.

Load in recorded voltage and control signals. First compare by eye to ensure that the two signals have some shared artifacts, e.g. a heartbeat artifact at 5-15 Hz or a motion artifact. Then search the traces for true signal, e.g. low frequency dynamics during and rest and sleep, or under ketamine-xylazine anesthesia. To un-mix the two signals, it is helpful if >25% of the variance of the signal trace consists of true signal. Next download FastICA or another ICA implementation. Use ICA to separate the signals. Examine the individual IC components, and compare the resulting traces to known artifacts and signal. If substantial hemodynamic artifact remains in the signal trace, create an estimate of the hemodynamic noise by fitting the signal trace with a sine wave of variable frequency and amplitude. Simultaneously un-mix the signal, reference, and control traces using ICA. Again look for artifacts in the signal trace. If substantial artifacts remain, try to increase reference channel expression by using transgenic reporter mice, raising viral titer (but not to the point that the virus is locally overexpressed), and injecting virus in multiple regions.

What is claimed:

1. A method comprising:
    delivering, to a target tissue, excitation light having a first wavelength and a second wavelength, wherein the target tissue contains a sensor and a reference;
    collecting optical domain responses from the sensor and the reference, the response from the sensor includes information pertaining to a biological parameter of interest as well as information pertaining to physiological artifacts and the response from the reference includes information pertaining to the physiological artifacts but not the biological parameter; and
    extracting the information pertaining to the biological parameter free of physiological artifacts.

2. The method of claim 1 wherein extracting a signal representative of a biological parameter further comprises unmixing the physiological artifacts from the response of the sensor using information contained in the response of the reference.

3. The method of claim 1 wherein delivering excitation light further comprises generating first light having the first wavelength from a first light source and generating second light having the second wavelength from a second light source.

4. The method of claim 3 and further comprising modulating the first light via a first modulation frequency.

5. The method of claim 4 and further comprising modulating the second light via the first modulation frequency and shifting phase of the second light relative to the first light.

6. The method of claim 3 and further comprising measuring the intensity of the first light and the second light.

7. The method of claim 1 wherein delivering excitation light to target tissue further comprises propagating the excitation light to a waveguide that is in optical communication with the target tissue.

8. The method of claim 7 wherein collecting optical domain responses from the sensor and the reference further comprises receiving the optical domain responses in the waveguide.

9. The method of claim 1 and further comprising separating the optical domain responses from the sensor and the reference.

10. The method of claim 1 and further comprising converting the optical domain responses from the sensor and the reference into electrical domain analogues thereof.

11. The method of claim 1 wherein extracting the information further comprises:
    generating an estimate of hemodynamic artifacts present in the response from the sensor; and
    generating a linear unmixing matrix for sorting the biological parameter of interest from the physiological artifacts using the estimate of hemodynamic artifacts.

12. The method of claim 11 wherein the linear unmixing matrix is generated using independent component analysis.

13. The method of claim 1 wherein the sensor is a first fluorescent protein and the reference is a second fluorescent protein.

14. The method of claim 1 wherein the biological parameter is membrane voltage of a neuron.

15. The method of claim 1 and further comprising delivering the sensor and the reference to the target tissue.

16. A system comprising:
- an excitation light subsystem, wherein the excitation light subsystem generates light having a first wavelength and a second wavelength, wherein the first wavelength is suitable for exciting fluorescence in a sensor, but not a reference, and the second wavelength is suitable for exciting fluorescence in the reference but not the sensor, and wherein fluorescence from the sensor contains information pertaining to a biological parameter of interest and physiological artifacts, including hemodynamic artifacts, and fluorescence from the reference contains information pertaining to the physiological artifacts, including hemodynamic artifacts, but not the biological parameter of interest;
- a waveguide for propagating the light to a target tissue and receiving fluorescence from the sensor and the reference;
- a signal processing subsystem comprising a processor that:
  (1) generates an estimate of hemodynamic artifacts;
  (2) extracts information pertaining to the biological parameter of interest free of any physiological artifacts by generating a linear unmixing matrix using the estimate of hemodynamic artifacts as an input.

17. The system of claim 16 wherein the linear unmixing matrix is generated using independent component analysis.

18. The system of claim 16 wherein the excitation light subsystem comprises a first laser for generating the light having the first wavelength and a second laser for generating the light having the second wavelength.

19. A method comprising:
- delivering a fluorescent sensor protein to a target tissue, wherein the sensor protein is responsive to a membrane voltage, hemodynamic artifacts, and motion artifacts;
- delivering a fluorescent reference protein to the target tissue, wherein the reference protein is responsive to the hemodynamic artifacts and the motion artifacts but not to membrane voltage;
- delivering excitation light to the target tissue to cause the sensor protein and the reference protein to fluoresce;
- collecting the fluorescence from the sensor protein and the reference protein;
- separating the fluorescence from the sensor protein and the reference protein;
- converting the fluorescence from the sensor protein to a first electrical signal and the fluorescence for the reference protein to a second electrical signal;
- estimating the hemodynamic artifacts present in the first electrical signal; and
- extracting a signal indicative of membrane voltage, free of hemodynamic and motion artifacts, using the estimate of hemodynamic artifacts and independent component analysis.

20. The method of claim 19 wherein the fluorescent sensor protein is MacQ-mCitrine and the fluorescent reference protein is mCherry.

* * * * *